United States Patent [19]

Viccaro et al.

[11] Patent Number: 5,427,770

[45] Date of Patent: * Jun. 27, 1995

[54] DENTIFRICES CONTAINING AMINO ALKYL SILICONES

[75] Inventors: John P. Viccaro, Whitestone, N.Y.; Samuel Lin, Paramus; Todd Domke, Clifton, both of N.J.; Alexander G. Ziemkiewicz, Spring Valley, N.Y.

[73] Assignee: Chesebrough-Ponds USA Co., Division of Conopco, Inc., Greenwich, Conn.

[*] Notice: The portion of the term of this patent subsequent to Jan. 7, 2009 has been disclaimed.

[21] Appl. No.: 4,489

[22] Filed: Jan. 14, 1993

Related U.S. Application Data

[63] Continuation of Ser. No. 276,704, Nov. 28, 1988, abandoned.

[51] Int. Cl.$^6$ .................. A61K 7/22; A61K 7/16; C08G 77/04; C07F 7/04
[52] U.S. Cl. .......................... 424/54; 424/49; 424/52; 106/35; 433/216; 523/105; 528/28; 528/38; 556/424
[58] Field of Search .............. 106/35; 424/49, 54, 424/52; 433/216; 523/105; 528/28, 38; 556/424

[56] References Cited

U.S. PATENT DOCUMENTS

| | | | |
|---|---|---|---|
| 2,806,184 | 9/1957 | Richter | 167/93 |
| 3,032,577 | 5/1962 | Morehouse | 260/448.2 |
| 3,389,160 | 6/1968 | Reid | 56/423 |
| 3,402,191 | 9/1968 | Morehouse | 260/448.2 |
| 3,507,955 | 4/1970 | Osipow | 424/54 |
| 3,544,948 | 12/1970 | Holdstock et al. | 260/29.2 |
| 3,597,955 | 4/1970 | Osipow | 424/54 |
| 3,624,120 | 11/1971 | Yetter | 260/488 |
| 3,852,075 | 12/1974 | Basadur | 106/11 |
| 3,860,709 | 1/1975 | Abbott et al. | 514/63 |
| 4,071,614 | 1/1978 | Grimm, III | 424/49 |
| 4,161,518 | 7/1979 | Wen et al. | 424/52 |
| 4,213,961 | 7/1980 | Curtis et al. | 424/54 |
| 4,243,658 | 1/1981 | Chang | 424/52 |
| 4,246,029 | 1/1981 | Saunders et al. | 106/3 |
| 4,256,731 | 3/1981 | Curtis et al. | 424/54 |
| 4,304,766 | 12/1981 | Chang | 424/52 |
| 4,430,235 | 2/1984 | Chu et al. | 252/49 |
| 4,450,152 | 5/1984 | Ona et al. | 424/70 |
| 4,454,110 | 6/1984 | Caslavsk | 424/54 |
| 4,485,090 | 11/1984 | Chang | 424/52 |
| 4,507,455 | 3/1985 | Tangney et al. | 528/26 |
| 4,510,127 | 4/1985 | Chang | 424/52 |
| 4,680,366 | 7/1987 | Tanaka | 528/27 |
| 5,078,988 | 1/1992 | Lin et al. | 424/49 |
| 5,154,915 | 10/1992 | Weber et al. | 424/54 |

FOREIGN PATENT DOCUMENTS

| | | |
|---|---|---|
| 689679 | 4/1953 | United Kingdom . |
| 1194885 | 6/1970 | United Kingdom . |
| 1447254 | 8/1976 | United Kingdom . |

OTHER PUBLICATIONS

European Search Report EP 89 20 2973.
PCT Appln. WO79/00454.
Chemical Abstracts; vol. 90; No. 16; 16 Apr. 1979, p. 612.
Seifen-Ole-Fette-Wachse, vol. 114, No. 2, 4th Feb. 1988, Augsburg, De, pp. 51–54.

Primary Examiner—Thurman K. Page
Assistant Examiner—Carlos Azpuru
Attorney, Agent, or Firm—Gerard J. McGowan, Jr.

[57] ABSTRACT

Dentifrices, including toothpaste creams and gels, and mouthwashes, are provided including aminoalkyl silicones. In the mouth, the aminoalkyl silicones form a lasting hydrophobic film on the teeth for prevention of cavities and stain. Antimicrobial compounds such as chlorhexidine may be included.

20 Claims, No Drawings

DENTIFRICES CONTAINING AMINO ALKYL SILICONES

This is a continuation application of Ser. No. 07/276,704, filed Nov. 28, 1988, now abandoned.

BACKGROUND OF THE INVENTION

Great strides have been made in recent years in the field of oral health care. However, much remains to be done. While the development of anticaries agents, especially the fluorides, has led to a decline in the incidence of tooth caries it is desirable to even further decrease the number of teeth affected thereby. Moreover, attention in the oral health care field has increasingly focused on the problems of gum disease, periodontitis. While antibacterial agents have been proposed for inclusion in products for use by consumers in the treatment of periodontitis, certain problems have been associated with their use. For example, use of chlorhexidine, which has been known as as antibacterial agent, has been associated with staining problems. It produces yellow to dark brown stains on teeth, tongue and oral mucosa. Furthermore, chlorhexidine has a very bitter taste.

There has been a need, therefore, for developing a dentifrice formulation including antibacterial agents, which does not cause staining of the teeth and which has an improved taste. Moreover, dentifrices having improved anticavity effects are also desirable.

Staining can be troublesome, whether or not chlorhexidine is the cause. The accumulation of stains on tooth surfaces poses an esthetic problem for many individuals. Stains are usually extrinsic in nature and generally represent discolorations of the pellicle and/or plaque. The exact mechanisms involved in stain formation are still obscure. It has been suggested that pigments produced by chromagenic bacteria, colored products from the chemical transformation of pellicle components and adsorption/retention of dietary constituents contribute to extrinsic stain formation. The dietary factors which appear to contribute heavily to stain accumulation include coffee, tea, and red wines, as well as smoking. In addition to chlorhexidine, staining is promoted by cationic antimicrobial agents such as hexetidine or quaternary ammonium compounds.

Plaque is a common factor in caries, gum disease and staining and greatly contributes to their development. Proper oral hygiene as currently practiced requires that plaque be removed or prevented not only for cosmetic purposes but also to eliminate a source of potential injury to teeth and gums.

Dental plaque is initiated when cariogenic bacteria adhere to pellicle, the proteinaceous film on the surface of teeth. These adherent bacteria metabolize dietary constituents, reproduce and accumulate to form the tenacious deposit known as, plaque. Plaque generally consists of bacteria, bacterial end products such as polysaccharides, inorganic salts and salivary proteins. Plaque bacteria ferment dietary carbohydrates to organic acids which demineralize enamel, resulting in tooth decay.

Plaque acts as a nucleus for the formation of calculus (tartar) which is essentially plaque that has been mineralized with calcium phosphate salts. As calculus matures and hardens, it tends to stain noticeably due to adsorption of dietary chromagens: tea, coffee, smoke, etc. In addition to their unattractive appearance, calculus deposits, at the gum line, are a contributing source of gingivitis and periodontal disease.

Silicones have previously been suggested for inclusion in dentifrice compositions in that it has been expected that they would coat the teeth and thereby prevent cavities and staining. For example, British Patent Specification 689,679 discloses a mouthwash containing an organopolysiloxane for the purpose of preventing adhesion of, or for removal of, tars, stains, tartar and food particles from the teeth. However, polymers such as those disclosed in the '679 specification, have not generally been successfully used for coating the teeth since it has been found that the polysiloxane does not adhere to the teeth for prolonged periods of time. Therefore, the need for dentifrice formulations including a hydrophobic substance which effectively coats the teeth has not been satisfied.

Yetter U.S. Pat. No. 3,624,120 discloses quaternary ammonium salts of cyclic siloxane polymers which are said to be useful as cationic surfactants, as bactericides and as anticariogenic agents. Yetter indicates that it is believed that the siloxane polymer absorbs on calcium phosphate to form a film which decreases the rate of acid solubilization. However, due to the solubility of the cyclic, surface active, low molecular weight, high N/Si ratio compounds of Yetter, it would not be expected that they could impart a lasting, strongly hydrophobic film to the surface of teeth. Moreover, there does not appear to be any disclosure in Yetter that its low molecular weight compounds would have any usefulness in preventing staining. Other problems with the Yetter compounds are their high cost due to the high N/Si ratio. Also, the freedom from toxicity of high N/Si ratio compounds may be questioned.

SUMMARY OF THE INVENTION

Applicants have discovered that dentifrices which include aminoalkyl silicones defined below form a hydrophobic barrier on the surface of teeth which is useful in preventing staining of teeth and in preventing cavities. The antistaining properties of the dentifrices of the invention are of particular significance when the compounds of the invention are used in conjunction with antimicrobials such as quaternary salts or bis biguanides such as chlorhexidine. In such event, the dentifrice provides the antistain and anticaries benefit of the aminoalkyl silicone together with the antibacterial and gum disease-fighting benefits of the quaternary ammonium salt or other antibacterial, without the usual disadvantage of staining. The antistaining properties of the amino alkyl silicones may likewise be of use when other staining compounds such as stannous fluoride are included in the dentifrices. In a preferred embodiment, the aminoalkyl silicones comprise amodimethicones. Also preferred are compounds having a molecular weight of about 5,000 and above and compounds which are non-cyclic.

The aminoalkyl silicones included in the dentifrice of the invention comprise two basic units, $$R^1{}_m R_n SiO_{(4-m-n)/2} \qquad (1)$$

wherein
$1 \leq m+n \leq 3$,
$1 \leq n \leq 3$,
$0 \leq m \leq 2$, where m and n are integers, and preferably
$m=2$,
$n=1$, and $$R^1{}_aR^2{}_bSiO_{(4-a-b)/2} \quad (2)$$

wherein $1 \leq a+b \leq 3$, where a and b are integers and wherein $R^1$ and $R^2$ are hydrocarbons or fluorinated hydrocarbons of 1 to 10 carbon atoms, hydroxy, alkoxy, hydrogen or acetoxy and R is

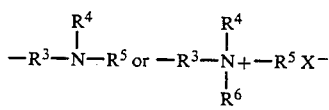

wherein $R^3$ is a divalent alkylene of 1 to 20 carbons optionally including 0 atoms, $R^4$, $R^5$ and $R^6$ may be different or the same and are selected from the group consisting of H, hydrocarbons of 1 to 20 carbons, and hydrocarbons of 1 to 20 carbons containing N and/or 0 atoms, preferably where the nitrogens are present as aliphatic amines and the oxygen atoms are present in hydroxyl groups, and $X^-$ is an anion preferably is selected from the group consisting of halide, hydroxide, tosylate and other monovalent anions. The amino alkyl silicones of the invention include 60% or fewer, by repeat unit, of unit (1). The aminoalkyl silicones of the invention may be linear, branched, random or block copolymers. Applicants have discovered that the above-defined aminoalkyl silicones when used in a dentifrice provide a hydrophobic film for the teeth which yields antistain and anticaries benefits.

The silicones of the invention have 60% or fewer repeat units of formula 1, more preferably 30% or fewer in order to combine acceptable substantivity of the film with modest cost and the absence of discoloration.

A particularly useful embodiment of the invention is a dentifrice which comprises a mixture of (I) an organosiloxane polymer which includes:
(a) at least one unit of formula 3,

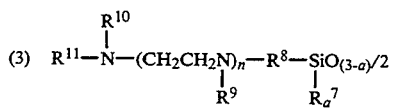

wherein:
a is from 0-2 and n is from 0-5,
$R^7$ is a monovalent radical,
$R^8$ is a divalent hydrocarbon radical,
$R^9$, $R^{10}$, and $R^{11}$ may be the same or different and are selected from the group consisting of H,

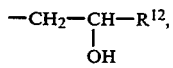

and $R^{12}$, where $R^{12}$ is a monovalent hydrocarbon or hydrogen, and
(b) at least one unit of formula 4, $$R_a{}^{13}R_c{}^{14}SiO_{(4-a-c)/2} \quad (4)$$

wherein $R^{13}$ and $R^{14}$ are the same or different monovalent radicals, a and c are integers selected from the group 0, 1, 2 and 3, and a plus c is 0, 1, 2 or 3, and (II) an orally acceptable antimicrobial compound other than (I), such as chlorhexidine. It is preferred that 60% or fewer repeat units of Formula 3, preferably 30% or fewer, are present in the molecule.

Although applicants do not wish to be limited to any Particular theory of operation of their invention, it is believed that when the aminoalkyl silicones come in contact with water of an appropriate pH, the nitrogens are protonated and the cations so formed are attracted to the negatively charged phosphate ions on the teeth. The hydrophilic charged moieties of the aminoalkyl silicones thus attracted to the teeth act as anchors for the hydrophobic alkyl silicone film which is thereby deposited onto the teeth and protects them from stain, caries, calculus and hypersensitivity.

The dentifrice of the invention can take several forms. It may, for instance, be a toothpaste cream or gel, or it may comprise a mouthwash; or it may be an oral spray, or chewing gum. In its preferred embodiment, the aminofunctional silicone of the invention (whether amodimethicones or other amino alkyl silicones,) is present in the form of an emulsion. As indicated above, in a particularly preferred embodiment of the invention, an antimicrobial such as a quaternary ammonium salt or a bis biguanide such as chlorhexidine is included in the dentifrice together with the aminofunctional silicone. Typical dentifrice ingredients may be included, depending, of course, on the form of the dentifrice. Toothpastes and gels will generally include surfactant, one or more abrasives and may include humectants. Toothpastes also contain other components such as alcohol, water, flavor, etc. Mouthwashes will generally include alcohol, water and humectant. The dentifrice may also take the form of a denture cleaner. In accordance with a further embodiment of the invention, mouthwashes are provided which include amino alkyl silicones and which can be formulated so as to be clear by matching the refractive index of the humectant and the amino alkyl silicone.

While the primary importance of the invention in the area of gum disease is believed to be the ability to use chlorhexidine or other antimicrobials such as quaternary ammonium compounds in a dentifrice without staining the teeth, it is believed that the compositions of the invention may be useful in prevention of gum disease by reducing or preventing plaque. Indeed, as indicated above, plaque is a common factor in caries, gum disease and staining and greatly contributes to the development of each of these problems.

It is our view that the positively charged nitrogen-containing silicones of the invention are attracted to negatively charges surfaces such as enamel so that silicones including alkyl amine groups are more substantive to the surface of the teeth. Moreover, increasing the number of aminoalkyl groups per molecule enhances the substantivity of the silicone. The increased substantivity of aminoalkyl-containing silicones enables them to impart a durable water repellent barrier to enamel which is compatible with cationic antimicrobial/antiplaque agents. Aminoalkyl silicones do not adversely affect the antiplaque activity of quats and/or bisbiquanides. On the other hand, while increasing the number of aminoalkyl groups per molecule should improve the association of the molecule with the surface of the tooth, it also tends to increase the solubility and reduce the hydrophobicity of the polymer. Consequently, it is preferred that the aminoalkyl groups constitute from 5 to 30% by repeat unit of the polymer. In other words, it is preferred that the number of silicon atoms which have nitrogen-containing moieties appended thereto constitute from 5 to 30% of the total number of silicon atoms.

While it is expected that the film of the alkylamino silicones of the invention will prevent the adhesion of staining materials such as chlorhexidine it is also believed that removal of such staining materials from the teeth will be facilitated thereby. Insofar as the dentifrices of the invention can reduce staining they would also provide a cosmetic as well as a health benefit. It is also contemplated that the compositions of the invention will reduce pain and progression of root caries via the coating action and will reduce unpleasant tastes from dental product components such as antimicrobials and surfactants, and will prevent calculus growths. Moreover, coating of hypersensitive areas may result in desensitization, etc.

The aminoalkyl silicones of the invention may be incorporated into dentifrices as oils as well as emulsions, but preferably as emulsions. The present invention also encompasses the process of applying the aminoalkyl silicones described herein onto the teeth, particularly in as an emulsion.

A preferred class of aminoalkyl silicone are the amodimethicones.

DETAILED DESCRIPTION OF THE INVENTION

The dentifrices of the invention preferably contain from 0.1 to 2% by weight, even more preferably from 1% to 5% by weight of the aminoalkyl silicones of the invention. The aminoalkyl silicones of the invention are non cyclic in general, and comprise two basic units of formulas 1 and 2 and may be linear, branched, random or block copolymers. Formulas 1 and 2 are as follows:

$$R^1_m R_n SiO_{(4-m-n)/2} \qquad (1)$$

wherein
$1 \leq m+n \leq 3$,
$1 \leq n \leq 3$,
$0 \leq m \leq 2$, where m and n are integers, preferably $m=2, n=1$ and $$R^1_a R^2_b SiO_{(4-a-b)/2} \qquad (2)$$

wherein
$1 \leq a+b \leq 3$, a and b are integers, and wherein
$R^1$ and $R^2$ are preferably hydrocarbons or fluorinated hydrocarbons of 1 to 10, even more preferably 1 to 4, carbon atoms. Examples include methyl, ethyl, phenyl, vinyl, trifluoropropyl and -cyanopropyl. Methyl and phenyl are preferred. $R^1$ and $R^2$ may also be hydroxyl, alkoxy, hydrogen, acetoxy or other reactive groups but their amounts are preferred to be low in order to promote adequate shelf stability.

R is defined as

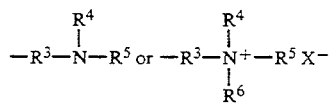

wherein $R^3$ is a divalent alkylene of 1 to 20 carbons optionally including 0 atoms, preferably 3 to 5 carbons. $R^4$, $R^5$ and $R^6$ may be different or the same and are H, hydrocarbons of 1 to 20 carbons, and hydrocarbons of 1 to 20 carbons containing N and/or 0 atoms. $R^4$, $R^5$ and $R^6$ preferably contain 1 to 10, even more preferably 1 to 4 carbon atoms. Examples are methyl, ethyl and phenyl.

X- is an anion preferably selected from the group consisting of halide, hydroxide, tosylate and other monovalent anions. Examples of R include:

$$-(CH_2)_3-NH_2,$$

$$-(CH_2)_3-NHCH_2CH_2NH_2,$$

$$-(CH_2)_3-O-CH_2-\overset{OH}{\underset{|}{C}H}-CH_2-NH_2,$$

$$-(CH_2)_3-\overset{\oplus}{N}H_3Cl^-,$$

$$-(CH_2)_3-\overset{Cl^-}{\underset{\oplus}{N}}(CH_3)_2(C_{18}H_{37}),$$

$$-(CH_2)_3-\overset{\oplus}{N}H_3OH^-$$

and $$-(CH_2)_3-N(CH_2CH_2OH)_2.$$

The concentration of formula (1) in the aminoalkyl siloxane polymer may range from 1% to 99% by repeat units, preferably from 1 to 60%, more preferably from 5 to 30%, and even more preferably from 5 to 10%. The preferred minimum molecular weight of the aminoalkyl silicone of the invention is 5,000. It is desirable that the molecular weight of the aminosilicones compounds be about 5,000 or greater since below 5,000 cyclization may occur and the compounds may dissolve in water. It is believed important that the silicones not be cyclized and not be soluble in order to permit them to deposit a lasting film onto the teeth. If the compounds are unduly soluble in water, it is believed that the film will too readily wash off the teeth.

There is no theoretical ceiling on the molecular weights of the silicones so long as they spread onto tooth enamel by brushing action or rinsing. Molecular weights will tend to fall within the range of 5,000 to 100,000, preferably 5,000 to 30,000. However, molecular weights may range as high as 1,000,000 or more are possible. Compounds with molecular weight from 10,000 to 30,000 would be expected to yield more substantive films than compounds having lower molecular weights. High molecular weight silicones are believed to form more stable films on the enamel surface whereas silicones of lower molecular weights tend to spread faster. Particularly preferred are dentifrices having average molecular weights of amino alkyl siloxane polymers in the ranges above. Silicones of high and low molecular weights may be mixed together to obtain mixtures of the desired viscosity. A viscosity for the aminoalkyl silicone in the range of 50 cps to 3,000 cps is preferred.

In the preferred embodiment the dentifrice preferably comprises a mixture including (I) from 0.01% to 20% by weight, even more preferably from 0.5% to 5% by weight of an organosiloxane polymer which includes:
(a) at least one unit of formula 3, $$(3) \quad R^{11}-\underset{R^9}{\underset{|}{N}}-(CH_2CH_2N)_n-\underset{R_a^7}{\underset{|}{R^8}}-SiO_{(3-a)/2}$$
$$\phantom{(3) \quad R^{11}-N}\underset{|}{\overset{R^{10}}{\phantom{N}}}$$

wherein:

a is from 0–2 and n is from 0–5, $R^7$ is a monovalent radical, $R^8$ is a divalent hydrocarbon radical, $R^9$, $R^{10}$, and $R^{11}$ may be the same or different and are selected from the group consisting of H, $$-CH_2-\underset{OH}{\underset{|}{CH}}-R^{12},$$

and $R^{12}$, where $R^{12}$ is a monovalent hydrocarbon radical or hydrogen, and (b) at least one unit of formula 4, $$R_a^{13}R_c^{14}SiO_{(4-a-c)/2} \quad (4)$$

wherein $R^{13}$ and $R^{14}$ are the same or different monovalent radicals, a and c are integers selected from the group of 0, 1, 2 and 3 and a plus c is 0, 1, 2 or 3, and (II) from 0.001% to 3% more preferably from 0.1 to 1% by weight of an orally acceptable antibacterial compound, such as a quaternary ammonium compound other than (I) or a bis biguanide such as chlorhexidine.

Each $R^7$ may independently be a hydrocarbon radical, a halogenated hydrocarbon radical, hydrogen, hydroxyl or alkenyl. Preferably, $R^7$ comprises from 1 to 10 and even 1 to 4 carbon atoms. Examples of $R^7$ are methyl, phenyl or -trifluoropropyl.

Each $R^8$ independently preferably comprises a divalent hydrocarbon radical having 3 or more carbons. Examples are propylene and butylene. Preferably $R^8$ does not exceed 10 carbon atoms.

$R^{12}$ is preferably selected from the group consisting of hydrogen, methyl or phenyl. Preferably $R^{12}$ includes 10 or fewer carbon atoms, more preferably, 4 or fewer.

Preferably $R^{13}$ and $R^{14}$ are independently selected from the group consisting of hydrocarbon radicals, halogenated hydrocarbons, hydrogen, hydroxyl and alkoxyls. It is preferred that $R^{13}$ and $R^{14}$ include from 1 to 10, preferably from 1 to 4 carbon atoms. Especially preferred $R^{13}$ and $R^{14}$ groupings are independently selected from the group consisting of methyl, phenyl and -trifluoropropyl.

Preferably a plus c is equal to 2.

The preferred antibacterial compound is chlorhexidine. Others include hexetidine, alexidine, quaternary ammonium antibacterial compounds and metal-ion containing antibacterial compounds mentioned later herein. The "quats" usually include a quaternary ammonium group having at least one long chain of carbon atoms attached thereto. The organopolysiloxane polymer comprising at least one unit of Formula 3 and one unit of Formula 4 may be used in a dentifrice according to the invention with or without the antibacterial compound.

Examples of Formula 3 are:

$$NH_2CH_2CH_2CH_2-\underset{CH_3}{\underset{|}{Si}}O-$$

and $$(HOCH_2CH_2)_2NCH_2CH_2-\underset{\underset{\underset{OH}{|}}{\underset{CH_2}{|}}}{\underset{CH_2}{\underset{|}{N}}}-\underset{CH_3}{\underset{|}{CH_2CH_2CH_2SiO}}-$$

The content of Formula 3 in the polymer ranges from 0.5% and up to 60% by repeat unit, preferably between 1 and 30%, more preferably from 5 to 15% by repeat unit. For reasons given above, the molecular weight is preferably above about 5,000.

The molecular weight of the preferred compound is preferably between 5,000 and 100,000, preferably between 5,000 and 30,000, although it may be as high as 1,000,000 or more. An example of such a polysiloxane is as follows:

$$Me_3Si(Me_2SiO)_{1000}(MeSiO)_{10}SiMe_3$$
$$\underset{\underset{\underset{CH_2CH_2-NH_2}{|}}{\underset{NH}{|}}}{\underset{(CH_2)_3}{|}}$$

Particularly preferred are compositions in which the organosiloxane polymer has an average molecular weight in the ranges above. As indicated earlier, the silicones may be incorporated into dentifrices as silicone oils (and then emulsified in the dentifrice) or as silicone emulsions, preferably as emulsions. Nonionic surfactants and/or cationic surfactants are preferred emulsifiers. Certain cationic quaternary ammonium surfactants such as tallow trimethylammonium chloride and cetyl pyridinium chloride may be used to advantage in that they also deliver anti-plaque health benefits in addition to being emulsifiers.

The amines of the invention become protonated and bear positive charges when the pH is below their pKas. Depending on structure, the pKas will range from about 7 to about 12. The pH of the dentifrices including the silicones of the invention should be below 10 and are preferably between 6 and 8 so that the aminoalkyl groups are protonated and degradation of the siloxane polymer is prevented.

The preferred dentifrices are toothpaste creams and gels, and mouthwashes. Ingredients which may be included in toothpastes and gels generally and which may be used in toothpaste and gel compositions in accordance with the invention are abrasive polishing materials, sudsing agents, flavoring agents, humectants, binders, sweetening agents, alcohol and water. Antitartar agents may be added to enhance the anticalculus affect of the present compositions.

Abrasives include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethylmethacrylate, powdered polyethylene, silica and the like. Depending on the form which the dentifrice is to take, the abrasive may be present in an amount of from 0 to 70% by weight, preferably from 1 to 70%, more preferably from 10 to 70% for toothpastes.

Humectants contemplated for use in the present invention include glycerol, polyol, sorbitol, polyethylene glycols and propylene glycol. The listed humectants are hydroxy functional compounds. The humectants are generally present in amounts of from 0 to 80%, preferably from 1 to 70%, more preferably 5 to 70%, by weight. Thickeners suitable for use in the invention include silica. Thickeners may be present in toothpaste creams and gels at 0.1 to 20% by weight. Binders suitable for use in the dentifrice of the invention include hydroxy ethyl cellulose (Natrasol) and hydroxypropyl cellulose (Klucel). It is preferred that anionic binders be avoided as it is believed that they complex with the amine cations of the aminoalkyl silicone. Binders may be present in the toothpaste of the invention to the extent of from 0.01 to 3% by weight. Sweeteners suitable for use in the present dentifrice, preferably at levels of about 0.1% to 5%, include saccharin. Alcohol is suitable for use in the present dentifrices, preferably at levels of about 0–5%, especially 0.5 to 5%, preferably 0.5 to 3%.

Certain pyrophosphate and other polyphosphate salts have been disclosed in U.S. Pat. Nos. 4,515,772 and 4,627,977 as being useful as antitartar agents. These include di- and tetra-alkali metal pyrophosphates wherein the alkali metals are preferably selected from the group consisting of sodium and potassium. Although phosphates are generally not favored as they tend to react with amino alkyl silicones, inclusion of these antitartar agents may be appropriate in certain formulations in accordance with our invention. Zinc salts are disclosed as anticalculus agents in U.S. Pat. No. 4,100,269 and in U.S. Pat. Nos. 4,416,867, 4,425,325 and 4,339,432 (with glycine). These antitartar agents may be included in the present formulations.

As discussed earlier in connection with emulsifying the silicone, it is generally preferred that surfactants (sudsing agents) used in the dentifrice of the invention be nonionic or cationic, although sarcosinate surfactants may be useful. Surfactants include polyoxypropylene-polyoxyethylene block copolymer, sorbitan stearate, sorbitan oleate, polysorbates, nonoxynols, sodium cocoylsarcosinate, sodium lauryl sarcosinate dimethyl cocamine oxide, dimethyl lauryl amine oxide and monolauryl citrate esters. Surfactants may be present within the range of 0 to 15%, preferably 0.1 to 15%, more preferably 0.25 to 10% by weight. Generally nonionic sudsing agents which may be suitable include condensation products of alkylene oxide groups with hydrophobic organic compounds such as alkyl phenols or the reaction products of propylene oxide and ethylene oxide diamine. Also included are the reaction products of ethylene oxide with aliphatic alcohols, long chain tertiary dialkyl sulfoxides. The cationic surfactants may be quaternary ammonium compounds including one $C_8$–$C_{18}$ alkyl chain. Examples include cetyl pyridinium chloride, cetyl trimethyl ammonium bromide, di isobutyl phenoxy ethoxy ethyl-dimethyl benzyl ammonium chloride and coconut alkyl trimethyl ammonium nitrate.

Hydrophilic silicones, such as those sold under the name SILWETS by Union Carbide, may be used in the present formulations.

Flavors are usually included in dentifrices in low amounts of e.g., 0.10% to 3%. Any type of flavor may be used. However, low- and nonaldehydic flavors are generally preferred since the amines of the silicones may otherwise react with the acyl groups of the aldehyde to form Schiff bases, which are colored and which would make the nitrogen atoms on the silicones unavailable for interaction with the surface of the tooth.

Fluoride sources used in toothpastes such as sodium fluoride, stannous fluoride, zinc ammonium fluoride, tin ammonium fluoride, calcium fluoride and cobalt ammonium fluoride may be included. Sodium monofluorophosphate may also be used, although it is not preferred as it tends to decrease deposition of the silicone. Since stannous fluoride tends to stain, its use together with the amino alkyl silicones of the invention may be particularly beneficial. Fluoride ions are typically provided at a level of from 50 to 1500 ppm, although higher levels up to, say, 3000 ppm may be used in the present dentifrices.

Casein and its hydrolysate are other potential anticaries agents, e.g., at a level of 0.1 to 5% by weight.

Titanium dioxide is a suitable whitener.

Dyes/colorants suitable for dentifrices, i.e. FD&C Blue #1, D&C Yellow #10, FD&C Red #40 etc. may be employed in the dentifrices of the invention.

Ingredients mentioned above as suitable for toothpastes are generally suitable for gels, as will be apparent to one of skill in the art of toothpaste and gel formulation. Thus, except where otherwise noted, references to toothpastes are to be construed as applying to gels as well.

Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 30% preferably from 0.5 to 30%. Nonionic and cationic surfactants are preferred.

The preferred clear mouthwashes of the invention comprise from 0.5 to 3% aminoalkylsilicone, preferably 1%, from 50 to 65% glycerol, preferably 50%, and from 0 to 2%. preferably 0.5 to 2%, more preferably 2%. However, other aminoalkylsilicone-containing formulations in which the refractive indexes of the ingredients are matched to form a clear mouthwash may be employed. The amodimethicone of Formula 5 below is preferred.

Where chlorhexidine and/or another antimicrobial compound are included in the dentifrice of the invention, the preferred concentration may range from 0.001% to 3%. Especially preferred concentrations range from 0.1% to 1%. Cetylpyridinium chloride, phenolics such as DP300 ex Ciba Geigy and salicylamides (including salicylanilides), and sources of certain metal ions such as zinc, copper, silver and stannous (e.g., zinc, copper and stannous chloride, and silver nitrate) may also be appropriate antibacterial agents.

Coburn et al., U.S. Pat. Nos. 4,358,443 and 4,287,191 describe the use of salicylamides and are incorporated by reference herein.

With the exception of the ethoxylated and propoxylated compounds discussed below, the aminoalkylsilicone compounds are for the most part known. Methods of preparing aminoalkylsilicones are given in, for example, Jex et al., U.S. Pat. No. 2,930,809 including U.S. application Ser. Nos. 555,201 (filed Dec. 23, 1955), and 555,203 (Filed Dec. 23, 1955), all of which are hereby incorporated by reference.

The aminoalkyl polysiloxanes of the invention may be end capped. If end capped, one or more of the end capping groups, $R_e$, preferably includes one or more nitrogen atoms. For example, $R_e$ may be $-(CH_2)_3NH_2$ or $-(CH_2)_3NHCH_2CH_2NH_2$.

As indicated above, a preferred class of aminoalkyl polysiloxanes is that of the amodimethicones. Amodimethicones are polydimethyl siloxane polymers containing aminoalkyl groups. The aminoalkyl groups may be, for example, n-propylamine or n-propyl-N-ethylenediamine and these may be present either pendant or at one or more ends of the polydimethylsiloxane chain. The amine groups cause the amodimethicone polymer to develop a net positive charge in aqueous systems over a wide range of pH say, from pH 1 to 10. Examples of amodimethicones include Dow Corning's DC-929, DC-Q2-7224, and Q2-8075. These polymers comprise aminoalkyl groups affixed to a predominantly polydimethysiloxane structure. The typical structure of Q2-8075's aminoalkyl group-containing units is:

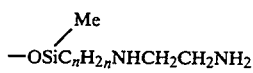

The amodimethicones useful in the present invention are exemplified by the formula which is shown in Formula 5, below:

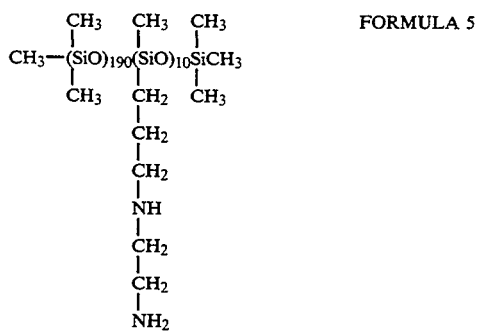

FORMULA 5

A special class of aminosilicones are ethoxylated and propoxylated aminosilicone compounds such as the following ethoxylated compound:

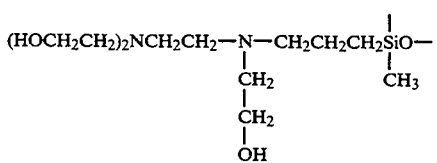

These have less of a tendency to react with aldehyde flavorants due to the presence of hydroxypropyl and hydroxyethyl groups. These compounds are described more fully in Lin et al. U.S. patent applications entitled "Dentifrices Including Modified Aminoalkyl Silicones", Ser. No. 07/276,719, filed Nov. 28, 1988, now U.S. Pat. No. 5,018,988 and "Hydroxylhydrocarbyl-modified Amino Alkyl Silicones", Ser. No. 07/276,726 filed Nov. 28, 1988, now abandoned, filed simultaneously herewith and incorporated by reference hereby.

Unless otherwise specified or required by the context, percentages of ingredients are by weight.

The following specific examples further illustrate the invention, but the invention is not limited thereto.

EXAMPLE 1

Since an important goal of the invention is to render surfaces of the teeth hydrophobic and corrosion resistant, the hydrophobicity imparted to surfaces by structurally different silicone polymers was investigated. Acid-cleaned, glass cover slips were incubated in whole human saliva to develop a pellicle thereon. After incubation, the cover slips were rinsed with distilled water and placed into a 3% silicone emulsion for 30 seconds. The cover slips were then rinsed with distilled water and contact angle measurements of water droplets on the slips were obtained with a goniometer. The contact angle between a surface and a water droplet is an indication of the hydrophobicity of the surface: the higher the contact angle the more hydrophobic the surface. The results obtained are given in Table I.

TABLE I

| Silicone Polymer | Molecular Weight | Viscosity | Mean Contact Angle (degrees) | Amine Content (wt %) |
|---|---|---|---|---|
| Dimethicones: | 6,600 | 100 cs | 22 | — |
|  | 19,000 | 500 cs | 19 | — |
|  | 26,000 | 1,000 cs | 10 | — |
| Amodimethicones: | 6,000 |  | 56 |  |
|  | *12,000 | 0.096 (intrinsic) | 71 | 0.6% |
|  | 15,000 |  | 55 |  |
|  | *18,000 | 0.128 (intrinsic) | 75 | 0.29% |
|  | 22,000 |  | 54 |  |
|  | *42,000 | 0.22 (intrinsic) | 75 | 0.15% |
| Dow Corning 929 |  |  | 57 |  |

*end capped with methoxy and N-2.aminoethyl-3-aminopropyl groups.

Since all of the oils investigated possessed a polydimethylsiloxane backbone, their inherent hydrophobicity would be expected to be similar. The foregoing data demonstrates that alkylamino silicones create a more hydrophobic surface, as compared to non-amino containing polysiloxanes. The data supports the concept that amino-functional groups increase the substantivity, i.e., affinity, of silicone based polymers.

EXAMPLE 2

Experiments were conducted to demonstrate that coating enamel with a substantive hydrophobic silicone film causes the enamel to be more resistant to attack from the organic acids produced by plaque bacteria and, therefore, to caries.

PROCEDURES:

Bovine incisors were cut, ground and polished so as to decrease enamel surface variables. A standard area (approx. 40 mm$^2$) was masked off and the teeth were painted. Upon removal of the mask, the exposed enamel surfaces were brushed with a 0.5% Triton X-100 solution to remove residual adhesive. All the teeth were rinsed and stored in distilled, deionized water until treated.

Emulsions were prepared containing 35% of the respective silicone polymer (See Table 2) and 6.9% Tergitol NP-10. These were diluted with distilled water to yield a final concentration of 3% silicone oil. Treatments consisted of a 1 minute brushing and a 9 minute soaking in the 3% silicone emulsions followed by a 10 second rinse with distilled water.

Treated teeth were placed into a 0.1M lactic acid buffer, pH 4.5, at 37° C. and shaken at 200 rpm. Aliquots of the buffer were removed at different time intervals up to 30 minutes and assayed for phosphorus using the Chen assay for the microdetermination of phosphorus in accordance with "Official Methods of Analysis, Association of Official Analytical Chemists," edited by Sidney Williams, Arlington, Va. p. 632 Percent reductions in acid dissolution rate were calculated by comparing the silicone-treated teeth to a water treated control set. The results are set forth in Table 2.

TABLE 2

ACID DISSOLUTION RESULTS OF SILICONE-TREATED BOVINE TEETH

| Silcone Polymer | Molecular Weight | % Reduction in Acid Dissolution | Mole % Alkyl-amine |
|---|---|---|---|
| Dimethicones: | | | |
| Union Carbide | LE-474 12,000 | 4.46 | 0.0 |
| | LE-460 28,000 | 9.85 | 0.0 |
| SWS Silicones | 100 cs 6,600 | 15.0 | 0.0 |
| SWS Silicones | 500 cs 19,000 | 5.2 | 0.0 |
| Petrach Sys. | 1000 cs 26,000 | 6.6 | 0.0 |
| Amodimethicones: | | | |
| (endcapped with methoxyl group | 12,000 | 27.3 | 2.5 |
| (endcapped with methoxyl group) | 18,000 | 25.6 | 1.6 |
| (endcapped with hydroxyl group) | 33.3 | low | |
| Endcapped, $R^1$ | 6,000 | 25.0 | 2.5 |
| | 15,000 | 21.3 | 1.0 |
| | 22,000 | 16.0 | 0.7 |
| Endcapped, $R^2$ | 19,000 | 24.2 | 0.8 |
| | 28,000 | 28.0 | 0.7 |
| Pendant, $R^1$ | 5,000 | 68.0 | 9.5 |
| | 15,000 | 47.9 | 3.0 |
| | 25,000 | 36.6 | 1.8 |
| Pendant, $R^2$ | 25,000 | 39.8 | 1.8 |
| $R^2$ = n-propylamine | | | |
| $R^1$ = n-propyl-N-ethylenediamine | | | |
| Dow Corning | 929 (pendant amines hydroxyl end groups) | 25.7 | low |
| | Q2-7224 | 10.4 | 2.0 |
| | Q2-8075 | 28.7 | 2.0 |
| Compound of Formula 5 (p. 20) | 15,000 mw | 53.0 | 5.0 |

DIMETHICONE (POLYDIMETHYLSILOXANE)

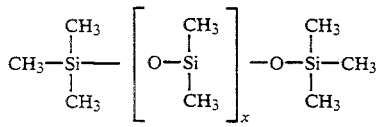

AMODIMETHICONES, END CAPPED

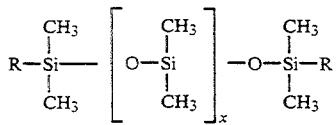

AMODIMETHICONE, PENDANT

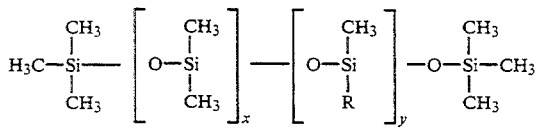

For $R^1$, R = $CH_2CH_2CH_2NH_2$

TABLE 2-continued

ACID DISSOLUTION RESULTS OF SILICONE-TREATED BOVINE TEETH

For $R^2$, R = $CH_2CH_2CH_2NHCH_2CH_2NH_2$

The contact angle data of Example I showed amodimethicones to be more substantive to a pellicle-coated surface than dimethicones. The acid dissolution data of the present example demonstrates the effectiveness of amino-functional silicones over alkyl silicones in depositing onto an enamel surface and in protecting it from caries.

Within the class of amodimethicones, it appears that those polymers having pendant alkylamines are more substantive to enamel and provide a better protective film than those having endcapping alkylamines. This increase in efficacy appears to be due to an overall increase in amine content (i.e., points for attachment). Indeed, the amodimethicones show a correlation between percent alkylamine and ability to reduce dissolution. Within the ranges of % alkylamine shown, an increase in alkylamine content tends to increase the % reduction in acid dissolution.

In the silicones with methoxy end caps, the methoxy group may further lend to the polymer's attachment to enamel through a covalent linkage thereby increasing polymer substantivity. The DC-929 is a commercially available emulsion of a polyalkyl silicone having low pendant amine content and hydroxyl end groups. Hydroxyl end groups may also enhance deposition in a manner similar to that of the methoxyl groups.

As a class, aminoalkyl silicones are more substantive to enamel than dimethicones. The most substantive amino silicone polymers are those which possess more than 3% alkylamine, pendantly attached to the polydimethylsiloxane backbone.

EXAMPLE 3

IN VITRO ANTIPLAQUE ACTIVITY OF A CHLORHEXIDINE/AMODIMETHICONE COMPOSITION

The intent of this study was to determine whether an amodimethicone polymer adversely affects the antiplaque activity of chlorhexidine.

PROCEDURE:

The antiplaque activities of chlorhexidine and chlorhexidine/amodimethicone solutions were determined by measuring the ability of these preparations to inhibit plaque production by *Streptococcus mutans* 6715-14 as follows:

Glass rods were suspended in a 1% sucrose-nutrient culture of S. mutans and incubated overnight at 36° C. The plaque-coated rods were removed the following day, rinsed with sterile water, immersed in a treatment solution (described below) for 30 seconds, rinsed with sterile water and subsequently placed in 3% sucrose-nutrient broth for six hours at 36° C. At the end of this period the rods were retreated with the treatment solutions as above, then placed in a 20% salvia supernatant solution and incubated overnight at 36° C. The following morning the rods were treated for a third time with the appropriate treatment solution as previously described, placed into a 3% sucrose-nutrient broth and again incubated for six hours at 36° C. Following this incubation period, the rods were rinsed with sterile water to remove residual medium and then completely dried in vacuum over phosphorus pentoxide. Plaque accumulation was determined by dry weight measurements as follows: the dried plaque coated rods were weighed, stripped of plaque with a 1N NaOH. The rods were subsequently rinsed with water and acetone and thoroughly dried at 110° C. The dried rods were weighed and plaque weights determined by difference.

The treatments were aqueous solutions containing 25% human saliva supernatant and the following agents at the indicated concentrations: a) water control, b) 0.20% chlorhexidine, c) 0.20% chlorhexidine/3.0% amodimethicone, d) 0.25% chlorhexidine, e) 0.25% chlorhexidine/3.0% amodimethicone. The amodimethicone employed was the compound of Formula 5 (page 20) which was emulsified with Tergitol surfactants and prepared as a 3.0% (w:v) emulsion.
RESULTS:

The treatment solutions containing only 0.20% and 0.25% chlorhexidine reduced plaque formation by 98% each. Similar reductions, of 97% and 99%, were respectively attained with the 0.20% and 0.25% chlorhexidine/amodimethicone solutions. The Formula 5 amodimethicone did not affect the antiplaque activity of chlorhexidine. These results coincide with those of prior experiments where commercially prepared amodimethicone emulsions containing tallowtrimethylammonium chloride and a solution of that quaternary compound both exhibited 70-75% reduction in plaque. Thus, amodimethicones, due to their cationic nature, are compatible with chlorhexidine and other cationic antimicrobials.

EXAMPLE 4

By virtue of their ability to coat enamel surfaces with a hydrophobic film, amodimethicones offer the opportunity of reducing natural or dietary stains as well as stains produced by cationic antimicrobial agents.

The object of this study is to demonstrate the ability of amodimethicones to reduce stain on bovine teeth and hydroxyapatite disks caused by dietary chromagens, e.g. coffee, tea, etc. Amodimethicone emulsions and an amodimethicone dentifrice were employed in the study.
PROCEDURE:

Bovine Teeth: Bovine incisors were cut into square slabs (approx. 1 cm$^2$) and mounted in acrylic plastic. The tooth surface was polished and its "whiteness" measured with a reflectometer. The enamel slabs were then placed into pooled human saliva and incubated at 36° C. for two hours, to form a pellicle on the tooth's surface. The teeth were rinsed with water, prior to treatment. Each slab was treated by brushing with a silicone emulsion for 30 seconds, followed by a 30 second soaking in the emulsion, rinsed with water and subsequently incubated in saliva for two hours at 36° C. This cycle of treatment and saliva soaking was repeated three times per day, ending with the slabs being incubated in saliva overnight. The following day the slabs were retreated three times as described above.

On the third day the treated slabs were stained by placing them in a tea/coffee solution for one minute, air dried, then soaked for one minute in ferrous ammonium sulfate solution, air dried, and ultimately immersed in human saliva for two hours at 36° C. This staining procedure was repeated seven times over a two day period. At the end of this period, the slabs were removed from the overnight soaking in saliva, air dried, and then lightly brushed with water (twenty strokes) to remove any loosely bound stain. All slabs were then air dried and their "whiteness" measured by a reflectometer. The difference in "whiteness" between the initial and final readings were employed to calculate percent stain reduction. The solutions employed in the above Procedure were 3.0% (w:v) emulsions of: a) Union Carbide LE-460 HS, 28,000 MW dimethicone emulsion; and b) a 5,000 MW amodimethicone containing 10% alkylamine groups emulsified with a Tergitol surfactant.

Disks Treated with Silicone Emulsions: Hydroxyapatite disks (29 mm diameter and 3 mm thickness) were prepared by pressing a mixture of hydroxyapatite powder and polyethylene powder (10%) in a hydraulic press. These disks were then heated at 110° C. overnight to enhance their firmness. The disks were submerged in the treatment silicone emulsions, brushed lightly for one minute, followed by a nine minute soaking period. The disks were then rinsed under running tap water and subsequently placed into a tea/coffee stain solution for one minute. Following this period, the disks were rinsed under running tap water, and during this rinsing the disks were lightly brushed until the stain was no longer removable. The disks were air dried and their "color" measured by a reflectometer using the CIELAb color scale and D65 illumination. The DE values obtained are a measure of the total color change as compared to a standard, in this case an unstained disk. As DE increases, so does the difference in color. The treatment solutions utilized in the above experiment were 3.0% emulsions of: a) the compound of Formula 5 emulsified with Tergitol surfactants; b) Petrarch 1000 cst dimethicone (26,000 Mw) emulsified with Tergitol surfactants; c) Union Carbide dimethicone LE 460 HS emulsion (28,000 MW); d) Union Carbide LE 474 dimethicone emulsion (12,000 MW).

Hydroxylapatite Disks Treated with Dentifrices:

The dentifrice treatments were employed as slurries, prepared by adding two parts of water and one part dentifrice. Hydroxyapatite disks were treated with the dentifrice slurries as described above with the silicone emulsions. The dentifrices used in this experiment were Topol, Colgate cream, Pepsodent and a silicone dentifrice containing 1.0% compound of Formula 5 (amodimethicone), alumina abrasive, gum thickener, surfactant, water, sorbitol liquid, saccharin and flavor.

RESULTS AND DISCUSSION

In the bovine teeth staining experiment (Table 3), both the dimethicone (LE 460 HS) and the 5,000 MW amodimethicone emulsions significantly reduced (95% confidence interval) the staining effects of the coffee/tea/iron salt mixture by 9.0% and 12.0% respectively, as compared to the water control. However, these reductions were not significantly different, most likely because of the difficulty of obtaining durable and reproducible stains on bovine teeth in vitro. Further antistaining experiments were conducted with pressed hydroxyapatite disks which, it was felt, better simulates the teeth for staining purposes.

The experiment conducted with hydroxyapatite disks and silicone emulsions showed that the amodimethicone's antistaining properties were superior to those delivered by the dimethicones tested (Table 4). The amodimethicone emulsion (Formula 5) inhibited stain by 50% while the dimethicone emulsions displayed stain reductions of 30-35%.

As can be seen in Table 5, the antistaining experiments conducted with hydroxyapatite disks and dentifrice slurries showed that the amodimethicone dentifrice formulation was far superior to the commercial products. The amodimethicone dentifrice reduced stain by 69%; by comparison, the best commercial dentifrice inhibited stain accumulation by less than 40%.

The present study reveals that amodimethicones are useful agents for preventing the staining of teeth caused by dietary chromagens, e.g. coffee and tea. Furthermore, amodimethicones displayed antistaining effects which were superior to those provided by dimethicones. Also, Table 5 shows that the antistaining qualities of an amodimethicone can be delivered from a dentifrice formulation.

TABLE 3

INHIBITION OF STAIN ON BOVINE ENAMEL

| Treatment | Delta L | Stain Inhibition, % |
|---|---|---|
| Water Control | −41.39 | — |
| LE 460 HS Dimethicone | −37.64 | 9.1 |
| 5,000 MW Amodimethicone | −36.44 | 12.0 |

Stain Inhibition = (1 − Delta L/Delta L control) × 100%

TABLE 4

INHIBITION OF STAIN ON HYDROXYAPATITE DISKS

| Treatment | DE | Stain Inhibition, % |
|---|---|---|
| Stained Control | 20.93 | — |
| Formula 5 Amodimethicone Dentifrice | 9.15 | 56.3 |
| LE 460 HS Dimethicone | 14.10 | 32.6 |
| LE 474 Dimethicone | 13.71 | 34.5 |
| 1000 cst Dimethicone | 14.66 | 30.0 |

Stain Inhibition = (1 − DE/DE control) × 100

TABLE 5

INHIBITION OF STAIN ON HYDROXYAPATITE DISKS

| Treatment | DE | Stain Inhibition, % |
|---|---|---|
| Stained Control | 26.86 | — |
| Amodimethicone (Formula 5) Dentifrice | 8.29 | 69.1 |
| Topol | 17.09 | 36.4 |
| Pepsodent | 20.41 | 24.0 |
| Colgate Cream | 19.00 | 29.3 |

Stain Inhibition = (1 − DE/DE control) × 100%

EXAMPLE 5

Anticaries property of aminosilicones as demonstrated by the dissolution test of hydroxyapatite powder.

In the concurrent exposure experiment hydroxyapatite powder was exposed in a pH 5 acetic acid solution which contained 5% silicone emulsion. In the sequential exposure experiments, the powder (3.5%) was first treated with a 5% silicone emulsion (60–70 ml) for ten minutes, filtered, washed with distilled water, and then exposed to 150 ml acetic acid solution. Aliquots were withdrawn at various time intervals and the solution filtered to remove hydroxyapatite powder. The amounts of phosphate ion in the liquids were measured by UV spectrophotometry at 710 nm with molybdate solution in accordance with Official Methods of Analysis, Association of Official Analytical Chemists, edited by Sidney Williams, Arlington, Va., p. 632. (1984). The results are shown in Table 6.

TABLE 6

ACID DISSOLUTION TESTS OF HYDROXYAPATITE POWDER WITH AMINOSILICONES
PPM Phosphate in Solution After

| | | 5 Min. | 10 Min. | 20 Min. | 30 Min. | 40 Min. | 50 Min. | 60 Min. |
|---|---|---|---|---|---|---|---|---|
| Concurrent exposure | Formula 5 aminosilicone | 0 | 0 | 45 | 93 | 16 | 78 | 54 |
| | Polydimethylsiloxane | 154 | 157 | 163 | 181 | 216 | 169 | 190 |
| Sequential exposure | Formula 5 aminosilicone | 22 | 90 | 104 | 109 | 113 | 131 | 122 |
| | Polydimethylsiloxane | 178 | 232 | 279 | 247 | 260 | 246 | 251 |
| *Untreated Hydroxy apatites | | 259 | 329 | 436 | 348 | 337 | 341 | 348 |

The experiment demonstrates that silicones decreased the rate of acid dissolution of hydroxyapatite powder and that the aminosilicones worked better than polydimethylsiloxane. For example, after 60 minutes exposure in the sequential experiment, the untreated powder dissolved 348 ppm phosphate ion into the solution, but only 122 ppm when they were treated with aminosilicones, and 251 ppm when treated with polydimethylsiloxane.

EXAMPLE 6-8

PREPARATION OF AMINO-CONTAINING SILOXANES

Reaction:

$$D_4 + [H_2NCH_2CH_2CH_2\underset{\underset{Me}{|}}{\overset{\overset{Me}{|}}{Si}}]_2\text{—O} \xrightarrow{(CH_3)_4N^+OH^-}$$

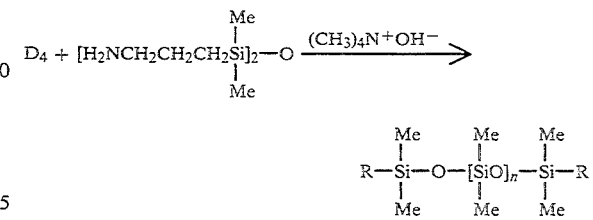

where $R = -(CH_2)_3-NH_2$

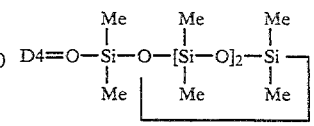

Reaction:

Into a 2 liter resin kettle equipped with mechanical stirrer (through a water-cooled joint), water condenser with argon inlet, and an additional funnel, was placed 1 kg of (SWS-03314) (ex. SWS Company, of Stauffer Chemical Company). It was stirred under a light argon flow to remove any air or moisture. 5.25 g of tetramethylammonium hydroxide (ex Aldrich) was added as the catalyst. 50.50 ml (45.3 g) of 1,3-Bis(3-aminopropyl)-1,1, 3,3-tetramethyldisiloxane (Petrarch, Silar) was added dropwise to the mixture. The contents were heated at 95°–100° C. for 20 hours and 2 hours at 150° C. The heating mantle was then removed and the mixture was allowed to cool to room temperature with stirring, under argon.

In order to remove excess amine and volatile components, the product was put on the rotary evaporator using vacuum first at room temperature and then heating to 85° C. for about an hour.

Characterization:

Bulk viscosity was measured to be 100 centistokes using a Brookfield viscometer. Intrinsic viscosity of solutions of the polymer in toluene were determined using an Ostwald tube and found to be 0.0605 dl/g.

Molecular weight was found by the Mark-Houwink equation, $[\eta]=KM^a$, where $a=0.66$ and $K=2\times10^{-4}$ for silicone polymers, to be 6000.

EXAMPLE 7: (MW 15000)

1043 g of D4, 5.3 g of tetramethylammonium hydroxide, and 15.71 g of 1,3-Bis(3-aminopropyl)-1,1,3, 3-tetramethylsiloxane were reacted together at 95°–110° C., as described in Example 6. Vacuum was used to purify the polymer product. Characterization procedures were the same as in Example 6. Bulk viscosity was 430 centistokes, intrinsic viscosity was 0.1155 dl/g, and MW was 15000.

EXAMPLE 8: (MW 22000)

1021 g of D4, 5.25 g of tetramethylammonium hydroxide, and 9.23 g of 1,3-Bis(3-aminopropyl)-1,1,3,3-tetramethylsiloxane were reacted together at 95°–100° C., followed by catalyst decomposition, as described in Example 6. The rotary evaporator was used to purify the product. Characterization procedures were the same as in example 6. The bulk viscosity was 1040 centistokes, the intrinsic viscosity was 0.1485 dl/g, and MW was 22000.

EXAMPLE 9

Siloxanes Containing Pendant Amines (MW 5000)

a) Synthesis of cyclic siloxanes containing amines

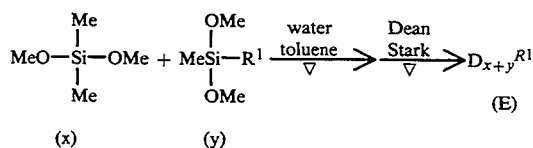

Into a 2 liter resin kettle equipped with mechanical stirrer, water condenser with argon inlet and addition funnel, was placed 350 g (x; 2.91 moles) of dimethyldimethoxysilane (Petrarch). Toluene (220 mls) was used as the solvent. 275.0 g (y; 1.33 moles) of aminoethylaminopropylmethyldimethoxysilane (Petrarch) was added followed by 2(x+y) moles Millipore water (152.6 g). The reaction was quite exotermic. When it cooled, it was heated at reflux temperature (71 C.) for 18½ hours. The Dean Stark condenser was used to remove the reaction by-products and solvents, and to drive the reaction to completion. A rotary evaporator was used to remove the rest of the toluene. A viscous slightly orange colored fluid was isolated as the product, (E). A 60 MHz NMR spectrum was used to determine the amount of amine present in the cyclic product, to be 1.1 amine group ($R^1$) per $D_3$ unit (or $D_4^{1.45R^1}$ in terms of $D_4$ for simplicity).

b) Preparation of 5000 MW siloxane with pendant amines

Reaction:

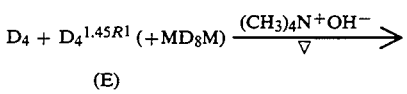

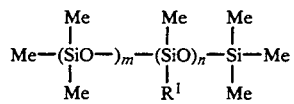

where $R^1 = (CH_2)_3NH(CH_2)_2NH_2$

Into a 2 liter resin kettle, equipped with water condenser, argon inlet, mechanical stirrer, addition funnel, and thermometer, was placed 380 g $D_4$(SWS), and 167.8 g $D_4^{1.45R^1}$ [(E) from part a]. 3.11 g $MD_8M$ (Dow Corning 2005 cs fluid), where $M=Me_3SiO_{0.5}$ and $D=Me_2SiO$, as end capper and tetramethylammonium hydroxide (Aldrich) were added. The reaction mixture was heated at 95° C. for 19 hours and then at 155° C. for 3 hours. Rotary evaporation removed the excess materials. The polymer was filtered to remove particulates.

Characterization of the polymer included measuring bulk viscosities using a Brookfield viscometer. The bulk viscosity was 120 cs. Since the viscosity-MW equations hold for siloxanes, but may not hold for siloxanes containing pendant amines, the MW was estimated from the stoichiometry of the reaction. The MW is approximately 5000, taking into account that this is an equilibrium polymerization with 10% excess volatile silicone before rotary evaporating. There are, on average, 6 pendant amines ($R^1$) per polymer. Example 10: Siloxanes containing pendant amines (MW 25000) ($R=CH_2CH_2CH_2NH_2$)

1035 g $D_4$, 62.2 g $D_4^{1.45R}$, 5.6 g of tetramethylammonium hydroxide catalyst, and 30.1 g of the $MD_8M$ endcapper were reacted together at 100° C. for 16 hours 150° C. for 2 hours and subjected to rotary evaporation. Bulk viscosity was found to be 540 cs. MW was estimated at 25000, with 6 pendant amines (R) per polymer.

EXAMPLES 11-19

Toothpaste Formulations Containing Chlorhexidine and Amodimethicones

All ingredients were added together or in sequence into a Hobart mixer and homogenized at room temperature or elevated temperature until the mixtures became homogenous pastes.

Toothpaste Formulations Containing Silicone Oil and Chlorhexidine Gluconate (Parts By weight)

| Ingredients | Ex. 11 | Ex. 12 | Ex. 13 | Ex. 14 | Ex. 15 | Ex. 16 | Ex. 17 | Ex. 18 | Ex. 19 |
|---|---|---|---|---|---|---|---|---|---|
| Natrosol 250M | 1.25 | 1.25 | 1.25 | — | — | — | — | — | — |
| Glycerin | 27 | 27 | 27 | 7 | 7 | 7 | 7 | 7.2 | 7.2 |
| Water | 5 | 5 | 5 | 15 | 15 | 15 | — | 11.3 | 11.3 |
| Kelcoloid S | — | — | — | 1 | 1 | 1 | 2 | — | — |
| Polyol III | — | — | — | 16 | 16 | 16 | — | 20.6 | 20.6 |

-continued

Toothpaste Formulations Containing Silicone Oil and Chlorhexidine Gluconate (Parts By weight)

| | Parts By Weight | | | | | | | | |
|---|---|---|---|---|---|---|---|---|---|
| | Ex. 11 | Ex. 12 | Ex. 13 | Ex. 14 | Ex. 15 | Ex. 16 | Ex. 17 | Ex. 18 | Ex. 19 |
| Sorbitol | — | — | — | — | — | — | 14 | — | — |
| Alumina 331 | 50 | 50 | 50 | 49 | 49 | 49 | 42.6 | 47.7 | 47.7 |
| $TiO_2$ | 0.5 | 0.5 | 0.5 | — | — | — | — | 0.5 | 0.5 |
| Pluronic F-87 | — | — | — | — | — | — | 4 | — | — |
| Hercules WSPM 1017 | — | — | — | — | — | — | — | 1.3 | 1.3 |
| Chlorhexidine-Gluconate | 4.25 | 4.25 | 4.25 | 4 | 4 | 4 | 4 | 4.1 | 4.1 |
| Flavor 77171 | 1 | 1 | 1 | 1 | 1 | 1 | 1 | 1 | 1 |
| Cpd. of Formula 5 | 4 | — | — | 2 | — | — | — | — | — |
| Cpd. of Formula 5 EO | — | — | 4 | — | — | 2 | — | — | 4.1 |
| Cpd. of Formula 5 PPO | — | 4 | — | — | 2 | — | 4 | 4.1 | — |
| Lauramine Oxide | 1 | 1 | 1 | — | — | — | — | — | — |
| Cocamine Oxide | 1 | 1 | 1 | — | — | — | — | — | — |
| Arlacel-80 | — | — | — | 1 | 1 | 1 | 1 | — | — |
| Tween-80 | — | — | — | 4 | 4 | 4 | — | — | — |
| Arlacel-60 | — | — | — | — | — | — | — | 0.9 | 0.9 |
| Tween-60 | — | — | — | — | — | — | — | 1.1 | 1.1 |
| Tergitol NP-15 | — | — | — | — | — | — | 0.5 | — | — |
| Water | 5 | 5 | 5 | — | — | — | 21 | — | — |

TABLE 6

Compounds for Exs. 11–38

| Trade Name | Chemical Name | | Supplier |
|---|---|---|---|
| Natrosol 250M | Hydroxyethylcellulose (nonionic water soluble polymer) | (Gum/Binder) | Hercules Inc. Wilmington, DE |
| Hercules WSPM 1017 | Experimental (Lauryl Cellulose Ether) | (Gum/Binder) | Hercules Inc. Wilmington, DE |
| Kelcoloid-S | Propylene Glycol Alginate | (Gum/Binder) | Kelco, Clark, NJ |
| Polyol III | A mixture of sorbitol and hydrogenated corn syrup | (Gum/Binder) | Lonza, Roquette Corporation |
| Alumina 331 | Hydrated Alumina ($Al_2O_3$) | (Abrasive) | Aluchem, Alcoa |
| Pluronic F-87 | Polyoxy Propylene Polyoxyethylene Block Copolymer | (Surfactant) | BASF-Wyandotte, Parsippany, N |
| Arlacel-80 | Sorbitan Oleate | (Surfactant) | ICI Americas |
| Tween-80 | Polysorbate-80 | (Surfactant) | ICI Americas |
| Tween-60 | Polysorbate-60 | (Surfactant) | ICI Americas |
| Tergitol NP-15 | Nonoxynol-15 [Polyoxyethylene(15)Nonyl Phenyl Ether] | (Surfactant) | Union Carbide |
| Titanium Dioxide | — | (Whitener) | Whitaker, Clark & Daniels |
| Flavor | — | (Flavor) | International Flavors & Fragrances (IFF) |
| Lauramine Oxide | Dimethylcocoamine Oxide | (Surfactant) | Armak Industrial Chem. Div. |
| Cocoamine Oxide | | | |
| PEG 1450 | Polyethyleneglycol (mw 1450) | (Humectant) | Union Carbide |
| Syloid 63X | Hydrated Silica (SiO) | (Abrasive) | W.R. Grace & Co. |
| Syloid 244 | Hydrated Silica (SiO) | (Thickener) | W.R. Grace & Co. |
| Hamposyl C-30 | Sodium Cocoylsarcosinate (30% w/w solution) | (Surfactant) | W.R. Grace & Co. |
| Hamposyl L-30 | Sodium Lauroylsarcosinate (30% w/w solution) | (Surfactant) | W.R. Grace & Co. |
| Hamposyl L-95 | Sodium Lauroylsarcosinate | (Surfactant) | W.R. Grace & Co. |
| Aromox DMMC-W | Dimethylcocoamine oxide | (Surfactant) | Armak Industrial Chem. Div. |
| Chlorhexidine Digluconate | Chlorhexidine digluconate (20% w/w solution) | (Active) | Lonza |
| Perillartine | — | (Sweetener) | Takasago Corp. |
| Flavor 2540 | — | (Flavor) | Formulated in house |
| Flavor 77171 | — | (Flavor) | Int'l Flavors Fragrances |

EXAMPLES 20–38

Toothpaste formulations were prepared by mixing the listed ingredients together. The toothpaste formulations were tested for reduction of acid dissolution as in Example 2. Results are given below.

SILICONE POLYMER DENTIFRICE FORMULATIONS

| | PARTS BY WEIGHT | | | | | | | |
|---|---|---|---|---|---|---|---|---|
| Ingredients | Ex. 20 | Ex. 21 | Ex. 22 | Ex. 23 | Ex. 24 | Ex. 25 | Ex. 26 | Ex. 27 |
| Natrosol 250M | 1.25 | 1.25 | 1.25 | 1.00 | 1.00 | 1.10 | 1.25 | 1.00 |
| Glycerin | 27.00 | 27.00 | 27.00 | 27.00 | 27.00 | 13.50 | 13.50 | 27.00 |
| Polyol III | — | — | — | — | — | 13.50 | 13.50 | — |
| Alumina 401 | 50.00 | 50.00 | 50.00 | 50.00 | 50.00 | 50.00 | 50.00 | 50.00 |
| Titanium Dioxide | 0.50 | 0.50 | 0.50 | 0.50 | 0.50 | 0.50 | 0.50 | 0.50 |
| Silicone Oil of FIG. 5 | 4.00 | 4.00 | 2.00 | 2.00 | 2.00 | 1.00 | 1.00 | 1.50 |
| Hamposyl C-30 | — | — | — | — | — | 3.33 | — | — |
| Hamposyl L-30 | — | — | — | 2.00 | — | — | 1.66 | 2.00 |
| Ammonyx DMCD-40 | — | — | — | — | — | — | — | — |
| Aromox DMMC-W | 2.00 | — | 1.00 | — | 2.00 | — | — | — |
| Arlacel 60 | — | 1.13 | — | — | — | — | — | — |
| Tween 60 | — | 1.37 | — | — | — | — | — | — |
| Chlorhexidine Digluconate | 4.00 | — | 4.00 | 4.00 | — | — | — | 4.00 |
| Sodium Fluoride | 0.10 | — | 0.10 | 0.20 | 0.20 | 0.20 | 0.20 | 0.20 |

SILICONE POLYMER DENTIFRICE FORMULATIONS

PARTS BY WEIGHT

| Ingredients | Ex. 20 | Ex. 21 | Ex. 22 | Ex. 23 | Ex. 24 | Ex. 25 | Ex. 26 | Ex. 27 |
|---|---|---|---|---|---|---|---|---|
| Aspartame | 0.30 | 0.30 | — | — | — | 0.30 | — | — |
| Perillartine | — | — | — | 0.10 | 0.10 | — | — | 0.10 |
| Sodium Saccharin | — | — | — | — | — | — | 0.20 | — |
| Flavor 2540 | 1.00 | — | — | 1.00 | 1.00 | 1.00 | 0.80 | 1.00 |
| Flavor 77171 | — | 1.00 | 1.00 | — | — | — | — | — |
| Distilled Water | 9.85 | 13.45 | 13.15 | 12.20 | 12.20 | 15.17 | 14.59 | 12.70 |
| 1 M Acetic Acid | — | — | — | — | — | 2.90 | 2.80 | — |
| 1 M HCl | — | — | — | — | — | — | — | — |
| pH | — | — | — | — | — | 7.32 | 7.24 | 9.71 |
| % Red. in Acid Diss. | 71.30 | 55.30 | 21.10 | 99.50 | 54.70 | 31.50 | 29.90 | 98.50 |

SILICONE POLYMER DENTIFRICE FORMULATIONS

PARTS BY WEIGHT

| Ingredients | Ex. 28 | Ex. 29 | Ex. 30 | Ex. 31 | Ex. 32 | Ex. 33 |
|---|---|---|---|---|---|---|
| Natrosol 250M | 1.00 | 1.00 | 1.00 | 1.10 | 1.10 | 1.10 |
| Glycerin | 27.00 | 27.00 | 27.00 | 27.00 | 27.00 | 27.00 |
| Alumina 401 | 50.00 | 50.00 | 50.00 | 50.00 | 50.00 | 50.00 |
| Titanium Dioxide | 0.50 | 0.50 | 0.50 | 0.50 | 0.50 | 0.50 |
| Silicone Oil of FIG. 5 | 1.00 | 1.00 | 2.00 | 2.00 | 2.00 | 4.00 |
| Hamposyl C-30 | — | — | — | 2.00 | — | — |
| Hamposyl L-30 | 2.00 | 2.00 | 2.00 | — | 3.33 | — |
| Hamposyl L-95 | — | — | — | — | — | 0.50 |
| Chlorhexidine Digluconate | 4.00 | 4.00 | — | — | — | — |
| Sodium Fluoride | 0.20 | 0.20 | 0.20 | 0.20 | 0.20 | 0.20 |
| Perillartine | 0.10 | 0.10 | — | — | — | — |
| Sodium Saccharin | — | — | 0.20 | 0.20 | 0.20 | 0.20 |
| Flavor 2540 | 1.00 | 1.00 | 1.00 | 1.00 | 1.00 | 1.00 |
| Distilled Water | 11.20 | 13.20 | 14.10 | 15.00 | 13.67 | 14.50 |
| 1 M Acetic Acid | 2.00 | — | — | — | — | — |
| 1 M HCl | — | — | 2.00 | — | — | — |
| 2 M HCl | — | — | 1.00 | 1.50 | 2.10 | 2.00 |
| pH | 7.66 | | 7.75 | 7.66 | 7.30 | 7.51 |
| % Red. in Acid Diss. | 46.50 | 99.00 | 53.50 | 49.50 | 38.40 | 52.00 |

SILICONE POLYMER DENTIFRICE FORMULATIONS

PARTS BY WEIGHT

| Ingredients | Ex. 34 | Ex. 35 | Ex. 36 | Ex. 37 | Ex. 38 |
|---|---|---|---|---|---|
| Natrosol 250M | 1.10 | 1.00 | 1.10 | 1.10 | 1.10 |
| Glycerin | 27.00 | 27.00 | 27.00 | 27.00 | 27.00 |
| PEG 1450 | — | — | 5.00 | — | 5.00 |
| Alumina 401 | 50.00 | — | — | — | — |
| Syloid 63X | — | 26.00 | 14.00 | 14.00 | 14.00 |
| Titanium Dioxide | 0.50 | 0.50 | 0.50 | 0.50 | 0.50 |
| Silicone Oil of FIG. 5 | 4.00 | 2.00 | 2.00 | 2.00 | 2.00 |
| Hamposyl L-30 | — | 2.00 | 2.00 | 2.00 | — |
| Hamposyl L-95 | 1.00 | — | — | — | — |
| Sodium Fluoride | — | 0.20 | 0.20 | 0.20 | 0.22 |
| Sodium Monofluorophosphate | 0.76 | — | — | — | — |
| Perillartine | — | 0.10 | 0.10 | 0.10 | — |
| Sodium Saccharin | — | — | — | — | 0.30 |
| Flavor 2540 | 1.00 | 1.00 | 1.00 | 1.00 | 1.00 |
| Distilled Water | 13.64 | 26.70 | 39.10 | 44.10 | 38.88 |
| 2 M HCl | 2.00 | — | — | — | — |
| pH | 7.01 | 7.17 | 7.78 | 7.53 | 7.77 |
| % Red. in Acid Diss. | 36.10 | 93.10 | 96.90 | 98.90 | 26.60 |

Formula 5 refers to the formula on page 20 of the specification. EO designates a compound which is ethoxylated in accordance with Lin et al. application entitled "Hydroxylhydrocarbyl-modified Aminoalkyl Silicones" filed simultaneously herewith mentioned above. Similarly PPO refers to the propoxlated compound. Ethoxylation or propoxylation of an aminoalkyl silicone yields a compound in which the primary amines become bonded to two $\beta$ hydroxy hydrocarbyl groups.

EXAMPLES 39–42

Mouthrinses

EXAMPLE 39

| INGREDIENT | wt % |
|---|---|
| Amodimethicone of FIG. 5 | 1.00 |
| Lauramine Oxide ex. Armak Aromox DMMC-W | 0.30 |
| Water | 45.84915 |
| 96% Glycerin USP | 50.00 |
| Ethanol | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

The mouthwash was made by dissolving 0.2% lauramine oxide in water. The amodimethicone was then added and emulsified. The emulsions thus prepared was added to glycerin and mixed. 0.1% lauramine oxide in ethanol was then dissolved in the mixture, flavor was added to ethanol and mixed, then added to the above mixture. The colors were added and mixed. Finally, chlorhexidine was added and mixed. A clear mouthwash resulted.

EXAMPLE 40

| INGREDIENT | CONC. % |
| --- | --- |
| 70% Sorbitol Soln. | 50.00 |
| Water | 43.69915 |
| Amodimethicone of FIG. 5 | 1.00 |
| Tergitol NP15 | 0.39 |
| Water | 2.06 |
| Ethanol (200PF) | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

The mouthwash was prepared as follows:

Sorbitol and water were mixed. The amodimethicone was emulsified with 0.09% tergitol and water and added to the sorbitol/water mixture. 0.30% tergitol was dissolved in ethanol and flavor was added. After mixing, the flavor mixture is added to the silicone emulsion. Colors were added and mixed. Finally, chlorhexidine was added and the preparation was mixed. A clear mouthwash was obtained.

EXAMPLE 41

| INGREDIENT | CONC. % |
| --- | --- |
| Amodimethicone of FIG. 5 | 2.00 |
| Lauramine Oxide ex. Armak Aromox DMMC-W | 0.30 |
| Water | 34.84915 |
| 96% Glycerin USP | 60.00 |
| Ethanol | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

0.2% lauramine oxide was dissolved in water. Amodimethicone was added and emulsified. The emulsions was added to glycerin and mixed. 0.1% lauramine oxide in ethanol was dissolved in the mixture. Flavor was added to ethanol and mixed, then added to the emulsion. Color was added and mixed. Chlorhexidine was added and mixed. A clear mouthwash was obtained.

EXAMPLE 42

| INGREDIENT | CONC. % |
| --- | --- |
| 96% Glycerin | 60.00 |
| Water | 34.29915 |
| Amodimethicone of FIG. 5 | 1.00 |
| Tergitol NP15 | 0.39 |
| Water | 2.06 |
| Ethanol (200PF) | 2.00 |
| Flavor | 0.25 |
| D&C Yellow #10 | 0.00060 |
| FD&C Blue #1 | 0.00025 |
| 20% Chlorhexidine Digluconate ex. Lonza Spectrodyne G. | 0.60 |

Sorbitol and water were mixed together. Amodimethicone was emulsified with 0.09% tergitol and 3.90% water and added to the sorbitol/water mixture and mixed. 0.30% tergitol was dissolved in ethanol, after which flavor is added and the mixture is mixed. The tergitol/ethanol/flavor was added to the emulsion after which colors were added and mixed. Finally, chlorhexidine was added and the preparation was mixed. A clear mouthwash resulted.

It should be understood that the specific forms of the invention herein illustrated and described are intended to be representative only. Changes, including but not limited to those suggested in this specification, may be made in the illustrated embodiments without departing from the clear teachings of the disclosures. Accordingly, reference should be made to the following appended claims in determining the full scope of the invention.

We claim:

1. A dentifrice comprising (a) a noncyclic, hydrophobic aminoalkyl silicone with a molecular weight of 5,000–1,000,000 of a formula comprised of two basic units:

$$R^1_m R_n SiO(4-m-n)/2 \qquad (1)$$

wherein $1 \leq m+n \leq 3$, $1 \leq n \leq 3$, $0 \leq m \leq 2$, and m and n are integers and $$R^1_a R_b^2 SiO(4-a-b)/2 \qquad (2)$$

wherein $1 \leq a+b \leq 3$, and a and b are integers wherein $R^1$ and $R^2$ are hydrocarbons or fluorinated hydrocarbons of 1 to 10 carbons, hydroxyl, alkoxyl, hydrogen or acetoxy, and R is $$-R^3-N\genfrac{}{}{0pt}{}{R^4}{R^5} \text{ or } -R^3-\overset{R^4}{\underset{R^6}{N^+}}-R^5 \ X^-$$

wherein $R^3$ is a divalent alkylene of 1–20 carbons or a hydrocarbon of 1–20 carbon atoms containing 0 atoms, $R^4$, $R^5$ and $R^6$ may be different or the same and are selected from the group consisting of H, hydrocarbons of 1–20 carbons, and hydrocarbons of 1–20 carbons containing N and/or 0 atoms, and $X^-$ is a monovalent anion, said aminoalkyl silicone including 60% or fewer by repeat unit of unit (1); and (b) an abrasive selected from the group consisting of alumina, hydrates thereof, magnesium trisilicate, magnesium carbonate, aluminosilicates, calcium carbonate, zirconium silicate, polymethylmethacrylate, powdered polyethylene, and silica, and (c) a humectant selected from the group consisting of glycerol, polyol, sorbitol, polyethylene glycols and propylene glycol.

2. The dentifrice according to claim 1 wherein $R^3$ is selected from the group consisting of:

$-(CH_2)_3-NH_2$ and $-(CH_2)_3-NHCH_2CH_2NH_2$.

3. The dentifrice of claim 1 wherein $R^1$ is selected from the group consisting of:

$$-(CH_2)_3-O-CH_2-\underset{OH}{CH}-CH_2-NH_2,$$

$$-(CH_2)_3-\overset{+}{N}H_3Cl^-, \ -(CH_2)_3-\overset{+}{N}(CH_3)_3Cl^-,$$

-continued

—(CH$_2$)$_3$—N$^+$(CH$_3$)$_2$(C$_{18}$H$_{37}$), and —(CH$_2$)$_3$—N$^+$H$_3$OH$^-$
Cl$^-$ 4. The toothpaste of claim 3 comprising from 0.1 to 20% by weight amino alkyl silicone, from 1 to 70% by weight abrasive, from 1 to 80% by weight humectant, from 0.1 to 3% by weight binder and from 0 to 3,000 ppm fluoride ion.

5. The dentifrice of claim 1 wherein the aminoalkyl silicone is an amodimethicone.

6. The dentifrice of claim 1 wherein from 5 to 30% of the repeating units are unit (1).

7. A dentifrice comprising (a) a noncyclic, hydrophobic aminoalkyl silicone with a molecular weight of 5,000–1,000,000 of a formula comprised of two basic units:

(1) R$^1$mRnSiO(4−m−n)/2 wherein 1≦m+n≦3, 1≦n≦3, 0≦m≦2, and m and n are integers and (2) R$^1$aR$^2$bSiO(4−a−b)/2 wherein 1≦a+b≦3, and a and b are integers wherein R$^1$ and R$^2$ are hydrocarbons or fluorinated hydrocarbons of 1 to 10 carbons, hydroxyl, alkoxyl, hydrogen or acetoxy, and R is

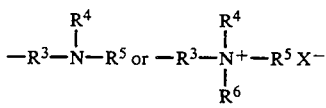

wherein R$^3$ is a divalent alkylene of 1–20 carbons or a hydrocarbon of 1–20 carbon atoms containing O atoms, R$^4$, R$^5$ and R$^6$ may be different or the same and are selected from the group consisting of H, hydrocarbons of 1–20 carbons, and hydrocarbons of 1–20 carbons containing N and/or O atoms, and X$^-$ is a monovalent anion, said aminoalkyl silicone including 60% or fewer by repeat unit of unit (1); and (b) an abrasive selected from the group consisting of alumina, hydrates thereof, magnesium trisilicate, magnesium carbonate, aluminosilicates, calcium carbonate, zirconium silicate, polymethylmethacrylate, powdered polyethylene, and silica and (c) a humectant selected from the group consisting of glycerol, polyol, sorbitol, polyethylene glycols and propylene glycol.

8. Dentifrice of claim 1 wherein the molecular weight is from 5,000 to 30,000.

9. A dentifrice which comprises a mixture of (i) a noncyclic, hydrophobic organosiloxane polymer with a molecular weight of 5,000–1,000,000 which includes:

(a) at least one unit of the formula (3),

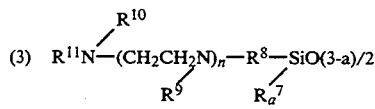

wherein:
a is from 0–2 and n is from 0–5,
R$^7$ is a monovalent radical,
R$^8$ is a divalent hydrocarbon radical,
R$^9$, R$^{10}$, and R$^{11}$ may be the same or different and are selected from the group consisting of R$^{12}$, where R$^{12}$ is a monovalent hydrocarbon or hydrogen, and (b) at least one unit of the formula 4, R$_a^{13}$R$_c^{14}$SiO(4−a−c)/2    (4)

wherein R$^{13}$ and R$^{14}$ are the same or different monovalent radicals, a and c are integers of the group selected from 0,1,2 and 3 and a plus c is 0,1,2 or 3, and (ii) an orally acceptable antimicrobial compound, said organosiloxane polymer including 60% or fewer by repeat units of unit (3); and (iii) an abrasive selected from the group consisting of alumina, hydrates thereof, magnesium trisilicate, magnesium carbonate, aluminosilicates, calcium carbonate, zirconium silicate, polymethylmethacrylate, powdered polyethylene, and silica and (iv) a humectant selected from the group consisting of glycerol, polyol, sorbitol, polyethylene glycols and propylene glycol.

10. The dentifrice of claim 9 wherein the organosiloxane polymer has a molecular weight of between 5000 and 100,000.

11. The dentifrice of claim 9 wherein the organopolysiloxane includes from 5 to 30% by repeat unit of formula (3).

12. A dentifrice which comprises a mixture of (i) a noncyclic, hydrophobic organosiloxane polymer with a molecular weight of 5,000–1,000,000 which includes:

(a) at least one unit of the formula (3),

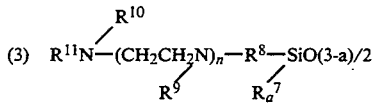

wherein:
a is from 0–2 and n is from 0–5,
R$^7$ is a monovalent radical,
R$^8$ is a divalent hydrocarbon radical,
R$^9$, R$^{10}$, and R$^{11}$ may be the same or different and are selected from the group consisting of R$^{12}$, where R$^{12}$ is a monovalent hydrocarbon or hydrogen, and (b) at least one unit of the formula (4), R$_a^{13}$R$_c^{14}$SiO(4−a−c)/2    (4)

wherein R13 and R14 are the same or different monovalent radicals, a and c are integers of the group selected from 0,1,2 and 3 and a plus c is 0,1,2 or 3, and (ii) an orally acceptable antimicrobial compound, said organosiloxane polymer including 60% or fewer by repeat units of unit (3); and (iii) a humectant selected from the group consisting of glycerol, polyol, sorbitol, polyethylene glycols and propylene glycol.

13. The dentifrice of claim 12 comprising a mouthwash including:
a) from 0.5 to 3% aminoalkyl silicone;
b) from 50 to 65% glycerol;
c) from 0 to 2% ethanol
wherein said mouthwash is clear.

14. A dentifrice comprising (a) a noncyclic, hydrophobic aminoalkyl silicone with a molecular weight of 5,000–1,000,000 of a formula comprised of two basic units:

R$_m^1$R$_n$SiO(4−m−n)/2    (1)

wherein 1≦m+n≦3, 1≦[,]n≦3, 0≦m≦2, and m and n are integers $$R_a^1R_b^2SiO(4-a-b)/2 \quad (2)$$

wherein $1 \leq a+b \leq 3$, and a and b are integers
wherein $R^1$ and $R^2$ are hydrocarbons or fluorinated hydrocarbons of 1 to 10 carbons, hydroxyl, alkoxyl, hydrogen or acetoxy, and R is

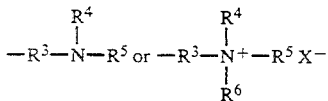

wherein $R^3$ is a divalent alkylene of 1–20 carbons or a hydrocarbon of 1–20 carbon atoms containing O atoms, $R^4$, $R^5$ and $R^6$ may be different or the same and are selected from the group consisting of H, hydrocarbons of 1–20 carbons, and hydrocarbons of 1–20 carbons containing N and/or O atoms, and $X^-$ is a monovalent anion, said aminoalkyl silicone including 60% or fewer by repeat unit of unit (1); and (b) a humectant selected from the group consisting of glycerol, polyol, sorbitol, polyethylene glycols and propylene glycol.

15. The dentifrice of claim 1, in the form of an emulsion.

16. The dentifrice according to claim 1 wherein the abrasives are selected from the group consisting of alpha alumina trihydrate, calcined aluminum silicate and aluminum silicate.

17. The dentifrice according to claim 7 wherein the abrasives are selected from the group consisting of alpha alumina trihydrate, calcined aluminum silicate and aluminum silicate.

18. A dentifrice which comprises a mixture of (1) a noncyclic, hydrophobic organosiloxane polymer with a molecular weight of 5,000–1,000,000 which includes:
(a) at least one unit of the formula (3),

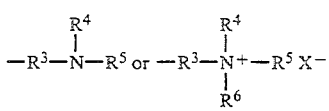

wherein:
 a is from 0–2 and n is from 0–5,
 $R^7$ is a monovalent radical,
 $R^8$ is a divalent hydrocarbon radical,
 $R^9$, $R^{10}$, and $R^{11}$ may be the same or different and are selected from the group consisting of $R^{12}$, where $R^{12}$ is a monovalent hydrocarbon or hydrogen, and
(b) at least one unit of the formula 4, $$R^{13}{}_aR^{14}{}_cSiO(4-a-c)/2 \quad (4)$$

wherein $R^{13}$ and $R^{14}$ are the same or different monovalent radicals, a and c are integers of the group selected from 0,1,2 and 3 and a plus c is 0,1,2 or 3, and (ii) an orally acceptable antimicrobial compound, said organosiloxane polymer including 60% or fewer by repeat units of unit (3); and (iii) a humectant which is selected from the group consisting of glycerol, polyol, sorbitol, polyethylene glycols and propylene glycol.

19. The dentifrice according to claim 18 further comprising an abrasive selected from the group consisting of alumina, hydrates thereof, magnesium trisilicate, magnesium carbonate, aluminosilicates, calcium carbonate, zirconium silicate, polymethylmethacrylate, powdered polyethylene, and silica.

20. A dentifrice comprising (a) a noncyclic, hydrophobic aminoalkyl silicone with a molecular weight of 5,000–1,000,000 of a formula comprised of two basic units:
 (1) $R^1{}_mR_nSiO(4-m-n)/2$ wherein $1 \leq m+n \leq 3$, $1 \leq n \leq 3$, $0 \leq m \leq 2$, and m and n are integers and
 (2) $R^1{}_aR^2{}_bSiO(4-a-b)/2$ wherein $1 \leq a+b \leq 3$, and a and b are integers
wherein $R^1$ and $R^2$ are hydrocarbons or fluorinated hydrocarbons of 1 to 10 carbons, hydroxyl, alkoxyl, hydrogen or acetoxy, and R is

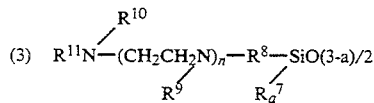

wherein $R^3$ is a divalent alkylene of 1–20 carbons or a hydrocarbon of 1–20 carbon atoms containing O atoms, $R^4$, $R^5$ and $R^6$ may be different or the same and are selected from the group consisting of H, hydrocarbons of 1–20 carbons, and hydrocarbons of 1–20 carbons containing N and/or O atoms, and $X^-$ is a monovalent anion, said aminoalkyl silicone including 60% or fewer by repeat unit of unit (1); and (b) a humectant which is selected from the group consisting of glycerol, polyol, sorbitol, polyethylene glycols and propylene glycol.

* * * * *